United States Patent [19]

Hatfield

[11] 3,953,440

[45] Apr. 27, 1976

[54] DEACETOXYCEPHALOSPORINS VIA PENICILLIN SULFOXIDE REARRANGEMENT

[75] Inventor: Lowell D. Hatfield, Indianapolis, Ind.

[73] Assignee: Eli Lilly and Company, Indianapolis, Ind.

[22] Filed: Dec. 13, 1974

[21] Appl. No.: 532,536

[52] U.S. Cl. .............................. 260/243 C; 424/246
[51] Int. Cl.² ....................................... C07D 501/10
[58] Field of Search ............................... 260/243 C

[56] References Cited
UNITED STATES PATENTS

| | | |
|---|---|---|
| 3,725,397 | 4/1973 | Graham et al. ................ 260/243 C |
| 3,725,399 | 4/1973 | Ellerton et al. ................ 260/243 C |
| 3,819,622 | 6/1974 | Cowley et al. ................ 260/243 C |
| 3,843,637 | 10/1974 | Rubinfeld et al. ............. 260/243 C |

*Primary Examiner*—Nicholas S. Rizzo
*Attorney, Agent, or Firm*—William B. Scanlon; Everet F. Smith

[57] ABSTRACT

Penicillin sulfoxides, notably the sulfoxides of penicillin V and penicillin G, are heated with amine salts of dichloromethane phosphonate in 1,1,2-trichloroethane to provide superior yields of deacetoxycephalosporins. The process is especially valuable in providing greater yields of the intermediate in the synthesis of the commercial antibiotic, cephalexin.

6 Claims, No Drawings

DEACETOXYCEPHALOSPORINS VIA PENICILLIN SULFOXIDE REARRANGEMENT

BACKGROUND OF THE INVENTION

This invention relates to a process for the preparation of deacetoxycephalosporins. In particular, it relates to an improved process for the conversion of penicillin sulfoxide esters to deacetoxycephalosporin esters.

In U.S. Pat. No. 3,275,626 Morin and Jackson describe the penicillin sulfoxide rearrangement reaction wherein the thiazolidine ring of a penicillin sulfoxide is expanded to the dihydrothiazine ring of the desacetoxycephalosporin. This process provided the first practical method for the preparation of the deacetoxycephalosporins, the 3-methyl-3-cephem compounds, and also povided for the first time a method for the preparation of cephalosporin compounds which did not depend upon cephalosporin C as a starting material.

In U.S. Pat. No. 3,647,787 Cooper describes an improved process for the conversion of penicillin sulfoxides to deacetoxycephalosporins which comprises heating the penicillin sulfoxide ester under acid conditions in a tertiary carboxamide, a urea derivative, and/or a sulfonamide. A further improved process is taught in U.S. Pat. No. 3,591,585 issued July 6, 1971. Therein the use of a sulfonic acid catalyst in a tertiary carboxamide solvent is described. More recently, U.S. Pat. No. 3,725,397 and U.S. Pat. No. 3,725,399 describe certain acid catalysts which can be employed in the ring expansion process. In the former patent, nitrogen base complexes formed with lower alkyl, phenyl lower alkyl, or phenyl dihydrogen phosphates are taught as useful acid catalysts in the rearrangement. The latter patent describes the use of certain amine salts of sulfonic acids, phosphorus acid, or trifluoroacetic acid in the ring expansion process.

The conversion of penicillin sulfoxide esters into deacetoxycephalosporins is the commercial method of choice for the preparation of the desacetoxycephalosporins. For example, the widely prescribed antibiotic, cephalexin, can be prepared from an intermediate 7-acylamidodeacetoxycephalosporanic acid ester prepared via the ring expansion of a penicillin sulfoxide ester. For example, a 6-acylamidopenicillanic acid ester sulfoxide such as an ester of 6-phenoxyacetamidopenicillanic acid sulfoxide is reacted under the ring expansion conditions to yield the corresponding ester of the 7-phenoxyacetamido-deacetoxycephalosporanic acid (an ester of 7-phenoxyacetamido-3-methyl-3-cephem-4-carboxylic acid). The 7-phenoxyacetyl side chain of the ring expanded cephalosporin product is then removed by employing the well known side chain cleavage reaction conditions to provide the cephalosporin nucleus ester, an ester of 7-amino-3-methyl-3-cephem-4-carboxylic acid. For example, the intermediate ring expanded ester can be reacted in an inert solvent with phosphorus pentachloride to form the imino chloride, which on reaction with a lower alkanol forms the unstable imino ether. The imino ether decomposes to effect N-deacylation of 7-phenoxyacetyl side chain with formation of the 7-amino nucleus ester. The nucleus ester is then acylated with a suitably protected phenylglycine derivative to provide the ester of 7-phenylglycylamido-3-methyl-3-cephem-4-carboxylic acid ester having the amino group in the 7-position side chain protected. The amino protecting group and the ester group of the $C_4$ carboxyl group are removed to provide the antibiotic cephalexin.

In view of the commercial importance of the antibiotic cephalexin, there exists a need for enhanced yields in the production thereof. One of the main steps in the overall process for the preparation of this antibiotic is the penicillin sulfoxide ring expansion reaction. Accordingly, improved yields of the intermediate deacetoxycephalosporin prepared by the ring expansion process would lead to enhanced yields in the production of the antibiotic.

SUMMARY OF THE INVENTION

This invention provides an improved penicillin sulfoxide ring expansion process. In particular, this invention provides an improved process for the production of deacetoxycephalosporins by the penicillin sulfoxide ring expansion process which comprises carrying out the process in the solvent, 1,1,2-trichloroethane, in the presence of a basic amine salt of dichloromethanephosphonic acid wherein the basic amine salt is formed with an amine selected from the group consisting of pyridine, quinoline, and isoquinoline, or the methyl substituted derivatives thereof. By employing the combination comprising the pyridinium, quinolinium, or isoquinolinium salts of the dichloromethanephosphonic acid with the unique solvent 1,1,2-trichloroethane, significantly greater yields of the ring expanded deacetoxycephalosporin products are obtained.

DETAILED DESCRIPTION OF THE INVENTION

According to the process of this invention, a 6-acylamidopenicillanic acid ester sulfoxide represented by the Formula I

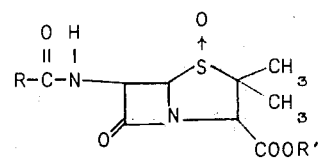

wherein R represents an acyl group derived from a carboxylic acid and R' represents a carboxylic acid protecting group, is heated in the solvent 1,1,2-trichloroethane in the presence of a salt of dichloromethanephosphonic acid formed with a cyclic tertiary amine base to provide a 7-acylamidodeacetoxy-cephalosporanic acid ester, (a 7-acylamido-3-methyl-3-cephem-4-carboxylic acid ester), represented by the following formula

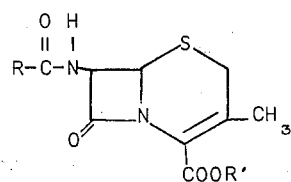

Cyclic tertiary amines which can be employed in the preparation of the dichloromethylphosphonate salts include pyridine, quinoline, isoquinoline, the lower alkyl substituted derivatives thereof such as 4-methylpyridine, 3-ethylpyridine, the methylated quinolines, the methylated isoquinolines, and like cyclic tertiary amines. The preferred salt in the present process is pyridinium dichloromethanephosphonate formed with dichloromethanephosphonic acid and pyridine. The salts of dichloromethanephosphonic acid are prepared by following the procedure described in U.S. Pat. No. 3,725,397 issued Apr. 3, 1973. These amine salts function as the acidic catalyst required in the rearrangement process as described by Morin and Jackson in U.S. Pat. No. 3,275,626.

The solvent, 1,1,2-trichloroethane, employed in conjunction with the above-named amine salts possess characteristics which make it uniquely suitable in the commercial scale penicillin sulfoxide rearrangement. For example, the boiling point of 1,1,2-trichloroethane is approximately 114°C. This boiling point provides a reaction temperature at reflux which allows the rearrangement to proceed in the reasonable short time of between 3 and 5 hours. Another key feature of this solvent which is employed to advantage in the rearrangement process is that it forms an azeotrope with water having a boiling point of 86°C. The azeotrope comprises approximately 16.4 percent water. Accordingly, the water of reaction is rapidly removed from the reaction mixture and prevents the formation of side products which otherwise would be formed should water remain for any substantial time in the reaction mixture. A further advantage of this particular solvent is that it is easily recovered in approximately 85 to 90 percent yields and, as recovered, can be reused. 1,1,2-Trichloroethane is a commercially available solvent which has the required stability for use in a commercial ring expansion process. Both the starting 6-acylamidopenicillanic acid ester sulfoxides and the rearrangement products, the desacetoxycephalosporin esters are soluble in the solvent. Further, the rearrangement product can generally be recovered with ease from the reaction mixture.

In carrying out the process of this invention, the respective concentrations of the penicillin sulfoxide and the amine salt in the reaction solvent, 1,1,2-trichloroethane can be varied. However, certain concentrations are preferred. For example, best yields are obtained when the penicillin sulfoxide concentration is approximately 0.05 to 0.5 molar and preferably about 0.11 molar, while the amine salt is present at a concentration of approximately 0.005 and 0.05 molar.

The process of this invention when carried out within the ranges of condition set forth above provides enhanced yields of the ring expanded cephalosporin rearrangement products. Generally, the increased yields realized vary between 5 and 10 percent greater than those yields reported in the art obtained with other acid catalysts and different solvents. These increased percentage yields represent very significant economic improvement over prior commercial processes.

The enhanced yields of deacetoxycephalosporins obtained by the practice of this invention are attributable at least in part to the elimination of side products which were customarily formed in prior ring expansion processes. For example, as taught by Morin and Jackson in U.S. Pat. No. 3,275,626, 7-acylamido-3-exomethylenecepham-4-carboxylic acid esters are among the cephalosporin substances produced in the described rearrangement. Also, the side product, 7-acylamido-3-hydroxy-3-methylcepham-4-carboxylic acid esters are formed. Both of these side products can generally be formed in significant amounts in the known ring expansion processes.

Table 1, below, lists the yields obtained with the preferred salt of this invention, namely, pyridinium dichloromethanephosphonate, employed in the rearrangement carried out in solvents described in U.S. Pat. No. 3,725,397. In the table, the yield data reported was obtained in the rearrangement of p-nitrobenzyl 6-phenoxyacetamidopenicillanic acid sulfoxide to p-nitrobenzyl 7-phenoxyacetamido-3-methyl-3-cephem-4-carboxylate. In each reaction with the listed solvent, the salt formed with dichloromethane phosphonic acid and pyridine was employed in the preferred concentration range of this invention.

TABLE I

Rearrangement of p-nitrobenzyl 6-phenoxyacetamidopenicillanic acid sulfoxide with pyridinium dichloromethanephosphonate in various solvents

| Solvent | Reaction Temp. (T°C.) | Time (hrs.) | Percent[1] Yield | M.P. °C[1] Product |
|---|---|---|---|---|
| Methyl isobutyl ketone | 116 | 2.5 | 72.4 | 183.5° |
| n-butyl acetate | 127 | 1 | 72.2 | 181.5–3.5 |
| dioxane | 101 | 10 | 75.5 | 185–7 |
| toluene | 111 | 4 | 74.3 | 187–9 |

[1]p-nitrobenzyl 7-phenoxymethyl-3-methyl-3-cephem-4-carboxylate.

The improved penicillin sulfoxide conversion process of this invention is applicable to the conversion of prior art penicillins. For example, those described in the art cited herein such as U.S. Pat. Nos. 3,275,626, 3,725,397, and 3,591,585. Exemplary of the penicillins which can be prepared or which are available for use in the process of this invention include the compounds of the above formula wherein R is lower alkyl, for example, methyl, ethyl, or heptyl; substituted alkyl, for example, cyanomethyl or chloromethyl; penicillins wherein R is benzyl, for example, penicillin G (benzyl penicillin), phenoxypenicillin (penicillin V), phenylmercaptopenicillin wherein R represents a phenylthiomethyl group; or R can be phenyl or substituted phenyl, for example, 6-benzamidopenicillin or 6-(2,6-dimethoxybenzamidopenicillin); or R could represent a heterocyclic methyl group such as 2-thienylmethyl, 2-furylmethyl, 3-thienylmethyl, and the like; or R can represent an α-substituted benzyl group represented by the formula

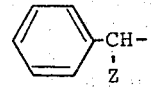

wherein Z represents an amino group substituted with a protecting group such as for example, a urethane protecting group as the t-butyloxycarbonyl group, the trichloroethoxycarbonyl group, the cyclohexyloxycarbonyl group, and like urethane groups; or other amino protecting groups such as the trityl group or a haloacetyl group such as chloroacetyl; or Z represents the carboxyl group or the sulfo group, —SO₃H, both of which are protected by esterification; or Z can be for example, the hydroxy group protected with a readily hydrolyzable hydroxy protecting group, for example the formyl group or the ester formed with a lower alkyl carboxylic acid for example, acetyl or propionyl, or a halogenated ester obtained with a halogenated lower alkanoic acid and the like. Other penicillins known in the art for example, "hetacycillin" and N- nitrosohetacycillin can also be employed in the process of this invention.

As is the case with the prior art processes for the conversion of the penicillin sulfoxides to the desacetoxycephalosporins, the penicillin starting material is employed in the form of an ester. A wide variety of penicillin esters are known and can be used in the instant process. The ester function serves to protect the carboxyl group during the heat induced acid catalyzed rearrangement and, therefore, ester groups are chosen from among those which are readily formed and which can be easily cleaved from the cephalosporin rearrangement product. Examples of easily cleaved ester groups which can be employed as the penicillin sulfoxide ester include for example, the halogenated hydrocarbon ester groups such as 2,2,2-trichloroethyl, the arylmethyl type such as benzyl, p-nitrobenzyl, 3,5-dimethoxybenzyl; the diarylmethyl types such as the diphenylmethyl(benzhydryl), the 3,5-dimethoxybenzhydryl, the 4,4-di-methoxybenzhydryl, and like esters; the imidomethyl esters for example, those represented when R' in the foregoing formula represents phthalimidomethyl or succinimidomethyl; the branched alkyl, alkenyl and alkynyl ester groups for example, the $C_4$ to $C_6$ t-alkyl ester groups such as tertiary-butyl and tertiary-pentyl, the $C_5$ to $C_7$-tertiary-alkenyl and the $C_5$ to $C_7$-tertiary alkynyl groups such as 1,1-dimethyl-2-propenyl, 1,1-dimethyl-2-butenyl, the 1,1-dimethyl-2-propynyl, the 1,1-dimethyl-2-pentynyl, and the like.

The penicillin nucleus, 6-aminopenicillanic acid (6-APA), is also a readily available penicillin starting material which can be employed in the improved process of this invention. When employed as a starting material, however, the 6-amino group and the $C_3$ carboxy group must be protected as with other penicillin starting materials having free amino groups. Protecting groups for the 6-amino group of 6-APA can be any of a wide variety of those employed in this art. For example, the protecting group can be a urethane, for example, tertiary butyloxycarbonyl, trichloroethoxycarbonyl, benzyloxycarbonyl, and the like. Also, the aryl methyl amino protecting groups, such as the trityl group can be employed. A further convenient protecting group for the 6-amino group of 6-APA is the formyl group represented in the foregoing formula when R represents hydrogen.

In carrying out the improved process of the present invention, it will be recognized by those skilled in the art that the 6-acylamido group of the penicillin starting material becomes the 7-acylamido side chain of the cephalosporin rearrangement product. If the 6-acylamido group of the penicillin is the desired side chain of the cephalosporin, removal of the ester group provides the desired product as the free acid. Alternatively, the 6-acylamido side chain of the penicillin starting material may be one chosen for reasons of convenience or of ready availability. In the latter case, this 6-acylamido side chain of the penicillin which following rearrangement is the 7-acylamido side chain of the desacetoxycephalosporin can be removed by the well known side chain cleavage reaction which employs a phosphorus halide such as phosphorus pentachloride as described by Chauvette in U.S. Pat. No. 3,549,628. Following the cleavage of the side chain, the resulting 7-aminodesacetoxycephalosporanic acid ester can be acylated in the 7-position with the chosen carboxylic acid to provide the desired 7-acylamidodesacetoxycephalosporin ester. The ester group can then be removed to provide the antibiotic compound.

Likewise, the 6-protected-aminopenicillanic acid ester formed by protecting the 6-amino group of 6-APA ester can be oxidized to form the sulfoxide, the sulfoxide rearranged in the process of this invention, and the 7-protected-aminodesacetoxycephalosporanic acid ester product can be deprotected, acylated with the desired carboxylic acid, and deesterified to provide the desired antibiotic compound.

In carrying out the process of this invention, the penicillin starting material, be it the 6-amino-protected penicillanic acid or the 6-acylamidopenicillanic acid, is first esterified to provide the $C_3$ protected carboxylic acid function and thereafter the ester is oxidized to form the sulfoxide. As is known in the art, penicillin sulfoxides are prepared by reacting the penicillin compound in an inert solvent with an inorganic oxidizing agent such as m-periodic acid, or preferably with an organic peracid such as peracetic acid, perbenzoic acid, or a substituted perbenzoic acid such as m-chloroperbenzoic acid.

According to the process of this invention, the 6-acylamidopenicillanic acid ester sulfoxide is dissolved or at least partially dissolved in 1,1,2-trichloroethane in an amount sufficient to achieve a concentration between 0.05 and .5 molar. The amine salt of the dichloromethane phosphonic acid is then added in an amount to achieve a concentration of between about 0.005 and 0.05 molar. The reaction mixture is then heated at the reflux temperature for between three and five hours. During the reflux period, the azeotrope formed with the solvent and water is collected in a water trap designed so as to return the heavier-than-water solvent back to the reaction vessel. Following the reaction, the mixture is cooled to room temperature and is concentrated, preferably in vacuo. On chilling or upon the addition of an organic liquid in which the reaction product is substantially insoluble, for example, methanol or ethanol, the reaction product precipitates. The reaction product is filtered, and is purified by recrystallization, if desired.

Although the process of this invention is preferably carried out at the reflux temperature of the reaction mixture, it can be carried out at temperatures between about 90° and 125°C. At temperatures below the reflux temperature, the reaction is allowed to continue for a longer time to insure completion and maximum yields. Reaction temperatures above the reflux temperature of 1,1,2-trichloroethane can be attained by operating above atmospheric pressure.

In a preferred embodiment of the present invention, p-nitrobenzyl 6-phenoxyacetamidophenicillanate sulfoxide is dissolved in 1,1,2-trichloroethane to achieve a concentration of approximately 0.11 molar and pyridinium dichloromethanephosphonate is added in an amount to achieve a concentration of .01 molar. The reaction mixture is then heated at the reflux temperature for 4 hours. During the reflux period, the water of reaction is distilled off as an azeotrope with the reaction solvent and is collected by means of a reflux condenser and a water trap. Following the reaction, the mixture is cooled to room temperature and is concentrated on a rotary evaporator. Ethanol is added to the concentrated reaction mixture to obtain the crystalline precipitate of p-nitrobenzyl 7-phenoxyacetamidodeacetoxycephalosporanate. The product is collected by filtration or other suitable means and is washed with ethanol and dried in vacuo.

In a further embodiment of the present invention, 2,2,2-trichloroethyl 6-phenylacetamidopenicillanate sulfoxide is dissolved in 1,1,2-trichloroethane to achieve a concentration of the sulfoxide of approximately 0.1 molar, and pyridinium dichloromethanephosphonate is added to the solution to achieve a concentration of approximately 0.01 molar. The reaction mixture is then heated at the reflux temperature for between 3 and 5 hours during which time the water of reaction is distilled as the azeotrope and is collected in a water trap. The reaction mixture is then cooled to room temperature and the solvent is evaporated to obtain a concentrated reaction product mixture. Alternatively, the reaction mixture can be evaporated to dryness to obtain the reaction product residue. The rearrangement product, 2,2,2-trichloroethyl 7-phenylacetamidodeacetoxy-cephalosporanate, is then purified by washing with a suitable solvent, for example methanol or ethanol, and can be further purified by recrystallization.

As previously mentioned, the rearrangement product, the deacetoxycephalosporanic acid ester, can be deesterified to obtain the deacetoxycephalosporanic acid when the desired side chain was employed in the 6-acylamidopenicillanic acid ester sulfoxide. When the rearrangement product does not have the desired 7-acylamido side chain, the rearrangement product is first reacted under the well known side chain cleavage reaction conditions to obtain the 7-aminodeacetoxycephalosporanic acid ester which is then acylated in the 7-position with a derivative of a carboxylic acid to obtain the desired cephalosporin ester. Thereafter, the acylation product is deesterified to provide the desired antibiotic.

The improved process of this invention comprising the unique combination of the solvent 1,1,2-trichloroethane and the acidic salts formed with tertiary cyclic amines and dichloromethanephosphonic acid provides improved yields of the deacetoxycephalosporanic acid esters. As shown in Table I, wherein yield data is presented for reactions employing a preferred acid salt catalyst of this invention with the solvents of the prior art, the yields obtained are significantly lower than those obtained in the present improved process employing 1,1,2-trichloroethane as solvent. Also, the yields obtained in the present process are significantly greater than those obtained by employing the amine salts of the acid catalysts described in U.S. Pat. No. 3,725,397.

The improved process of this invention is particularly valuable in the preparation of the commercial antibiotic cephalexin. Cephalexin can be prepared in a multi-step process which comprises the rearrangement of an ester of penicillin V sulfoxide. The rearranged ester, an ester of 7-phenoxyacetamido-3-methyl-3-cephem-4-carboxylic acid, is the subjected to the side chain cleavage reaction to provide the nucleus 7-amino-3-methyl-3-cephem-4-carboxylic acid ester which is then acylated with an amino protected D-phenylglycine derivative to provide the amino protected cephalexin ester. The amino protecting group and the ester group are removed to provide cephalexin. In this multi-step process for the production of commercial quantities of the valuable antibiotic cephalexin, the significant yield advantage realized by carrying out the ring expansion process of this invention provides enhanced yields of the antibiotics.

In order to further illustrate the improvements and procedures of this invention, the following examples are provided.

EXAMPLE 1

Preparation of Pyridinium Dichloromethanephosphonate

A well stirred mixture of 32 ml. (0.4M) of chloroform, 17.6 ml. (0.2M) of phosphorus trichloride and 53.6 g. (0.4M) of aluminum chloride was refluxed for two hours and thereafter was cooled to room temperature. The reaction mixture was poured into 140 ml. of methylene dichloride and the solution was cooled to −30°C. With vigorous stirring 52 ml. of water (2.88M) were added dropwise while the temperature was maintained below 5°C. Following the addition of the water the reaction mixture was warmed to about 20°C. and was stirred for one-half hour. The hexahydrate of aluminum chloride which formed as a precipitate was filtered and was washed on the filter 3 times with 100 ml. portions of methylene chloride. The washes were combined with the filtrate. Water (8 ml., 0.44M) was added to the mixture which was then refluxed for one hour and then allowed to stand overnight. The reaction mixture was evaporated on a rotary evaporator to remove the methylene dichloride. The solid residue was dissolved in 100 ml. of acetone and the acetone was removed by evaporation. The residual pale yellow syrup was dissolved in 100 ml. of acetone and the solvent again removed by evaporation on a rotary evaporator. The syrup was redissolved in 100 ml. of acetone and the solution chilled to 0°C. Approximately 16 ml. of pyridine were added dropwise to the cold solution until no further precipitate was formed. The heavy, granular, white crystals of pyridinium dichloromethane phosphonate were filtered and washed with acetone. The salt was dried in vacuo to yield 40.54 g. of white, granular crystals which represented an 83.1 percent yield. The salt was free of ionic chloride as shown in the silver nitrate test.

EXAMPLE 2

Ring Expansion with Pyridinium Dichloromethanephosphonate in 1,1,2-trichloroethane To a 300 ml. round bottom 3-neck flask equipped with a thermometer, a reflux condenser, and a Dean-Stark trap were added 88 ml. of 1,1,2-trichloroethane, 5.0 g. (10 mM.) of p-nitrobenzyl 6-phenoxyacetamidopenicillanate sulfoxide and 0.25 g. (1 mM.) of pyrridinium dichloromethanephosphonate. The reaction mixture was heated at the reflux temperature of 114°C. for 4 hours. During the reflux period, approximately 0.2 ml. of water were collected in the water trap. Following the reaction, the mixture was cooled to room temperature and concentrated in a rotary evaporator, warmed in a water bath at a temperature of 40°–50°C. to a residue weight of about 10–15 g. The solvent, 1,1,2-trichloroethane was collected and retained for reuse. Approximately a 90 percent recovery of the solvent was realized.

The reaction product residue was crystallized by the addition of 50 ml. of 3A alcohol with virogous stirring. The crystalline product, p-nitrobenzyl 7-phenoxyacetamidodeacetoxycephalosporanate, was filtered and washed on the filter with 50 ml. 3A alcohol. The washed product was then dried in vacuo at 50°–60°C. to a constant weight. The yield of product obtained was 4.21 g. (87.0 percent yield). The product melted at about 188°–189°C.

EXAMPLE 3

To a solution of 10.0 g. of p-nitrobenzyl 6-phenylacetamidopenicillanate sulfoxide in 175 ml. of 1,1,2-trichloroethane was added 0.5 g. (2 mM) of pyridinium dichloromethanephosphonate and the mixture was heated for 3 hours at the reflux temperature. The reaction mixture was concentrated under reduced pressure to a weight of about 28 g. and 100 ml. of methanol were added to the concentrate. The diluted concentrate was cooled to 0°C. and the precipitated product was collected by filtration. The product was washed on the filter with 60 ml. of cold methanol and air dried. The yield of the product, p-nitrobenzyl 7-phenylacetamidodeacetoxycephalosporanate, thus obtained was 7.87 g. (81.7 percent yield) as a white solid melting at 226°–226.5°C.

Thin layer chromatography of the filtrate of the diluted reaction mixture showed at least 5 percent additional product was contained in the filtrate.

I claim:

1. In the process for preparing a 7-acylamido-3-methyl-3-cephem-4-carboxylic acid ester by heating a 6-acylamidopenicillanic acid ester sulfoxide in an inert solvent in the presence of an acidic catalyst, the improvement which comprises heating the penicillin sulfoxide in 1,1,2-trichloroethane in the presence of an amine salt of dichloromethanephosphonic acid wherein the amine salt is formed with an amine selected from the group consisting of pyridine, quinoline, isoquinoline and the methyl substituted derivatives thereof.

2. The process of claim 1 wherein the penicillin sulfoxide ester in p-nitrobenzyl 6-phenoxyacetamidopenicillanate sulfoxide.

3. The process of claim 1 wherein the penicillin sulfoxide ester is p-nitrobenzyl 6-phenylacetamidopenicillanate sulfoxide.

4. The process of claim 1 wherein the penicillin sulfoxide ester is 2,2,2-trichloroethyl 6-phenylacetamidopenicillanate sulfoxide.

5. The process of claim 1 wherein the amine salt is pyridinium dichloromethanephosphonate.

6. The process of claim 1 wherein the amine salt is present at a concentration of between 0.005 and 0.05 molar while the penicillin sulfoxide ester is present at a concentration of between 0.05 and 0.5 molar.

* * * * *